United States Patent [19]
Baldwin

[11] Patent Number: 5,833,971
[45] Date of Patent: Nov. 10, 1998

[54] PERFUMED ROCKS

[76] Inventor: Stanley Baldwin, 636 E. 92nd St., Brooklyn, N.Y. 11236

[21] Appl. No.: 876,301

[22] Filed: Jun. 16, 1997

[51] Int. Cl.$^6$ ....................................................... A61K 7/36
[52] U.S. Cl. ........................ 424/76.4; 424/401; 424/76.9
[58] Field of Search ................................. 424/401, 76.4, 424/76.9

[56] References Cited

U.S. PATENT DOCUMENTS

| | | | |
|---|---|---|---|
| 2,544,093 | 3/1951 | Kilgore | 167/22 |
| 4,172,123 | 10/1979 | Lowicki | 424/67 |
| 5,620,693 | 4/1997 | Piot et al. | 424/401 |

*Primary Examiner*—Thurman K. Page
*Assistant Examiner*—Kathryne E. Shelborne

[57] ABSTRACT

A solid air freshener dispensing system (10) having a wax containing fragrance (16). Magnesium Silicate Hydrate (18) is mixed into the wax. When the solid air freshener dispensing system (10) is exposed to air the fragrance (16) is released. The solid air freshener dispensing system (10) is packaged in a container filled with an inert gas that retards the releasing of the fragrance (16).

19 Claims, 2 Drawing Sheets

LIST OF INGREDIENTS 14.00% Fragrance (16)

20.00% Magnezium Silicate Hydrate (18)

27.50% Saturated Monobase Acid (20)

27.50% Hydrogenated Castor Wax (22)

3.00% Carnuba Wax (24)

1.00% Montan Wax (26)

7.00% Metazene (28)

LIST OF INGREDIENTS 14.00% Fragrance (16)

20.00% Magnezium Silicate Hydrate (18)

27.50% Saturated Monobase Acid (20)

27.50% Hydrogenated Castor Wax (22)

3.00% Carnuba Wax (24)

1.00% Montan Wax (26)

7.00% Metazene (28)

FIG. 2

PERFUMED ROCKS

BACKGROUND OF THE INVENTION

1. Field of the Invention

The present invention relates to air freshening. More particularly, the present invention relates to chemical compound which releases an air freshening material.

2. Description of the Prior Art

Air fresheners have been developed with various ingredients which release deodorizing chemicals into the air. The releasing means typically are evaporated from a wick like device having a reservoir or a discharge of an atomizing mist from a spray container. The reservoir and wick means requires that a wick device be exposed. The air freshener is automatically released once the wick is exposed. Because the evaporation rate of the air freshener is dependent on the humidity of the air, the amount of an air freshener released into the air varies. Further, the liquid in the reservoir is subject to spillage during shipping and use. The spray means typically results in a short term freshening of the air as the droplets are rapidly dispersed. The air freshener is manually released. What is desired is an air freshener, that automatically releases into the air, and is cosmetically pleasing in design and overcomes the risk of spillage.

Numerous innovations for air fresheners have been provided in the prior art that are described as follows. Even though these innovations may be suitable for the specific individual purposes to which they address, they differ from the present invention as hereinafter contrasted.

In U.S. Pat. No. 5,587,174, titled Cosmetic Composition for Treating Skin and Hair Containing Apple Wax and Methods of Making Them, invented by Gunther Lang, Dieter Hoch, Eugen Kourad, Wolfram Geibel, Harald Wendel and Thomas Kripp, the skin and hair treatment composition includes 0.5 to 2 percent by weight apple wax, 0.1 to 30 percent by weight of at least one anionic, cationic, amphoteric and/or nonionic surfactant, a solvent consisting of water, ethanol, propanol, isopropanol, glycols or mixtures thereof and one or more cosmetic additives selected from the group consisting of perfume oils; opacifiers; pearlescing agents; bacterial and fungicidal ingredients; coconut fatty acid diethanolamide; buffer substances; coloring materials; solubilizers; light stabilizers; antioxidants; complexing agents and antidandruff active ingredients. Methods for obtaining the apple wax used in these compositions include extraction of depectinized apple pomace with a variety of solvents and purification and evaporation of the extract to obtain an apple wax product.

The patented invention differs from the present invention because the patented invention is a composition consisting of 0.5 to 2 percent of apple wax, 0.1 to 30% percent of at least one surfactant a solvent, and additive. The patented invention is in the form of an emulsion, cream or gel. The present invention is a chemical compound comprising a solid which contains an active ingredient within a matrix. The active ingredient migrates from the reservoir of the solid to the surface of the matrix where it absorbs and masks odors. The composition of the solid and the matrix is shown above. The rate of release is controlled by the addition of a control substance consisting of, hydrogenated castor wax, carnauba wax, montan wax, and magnesium.

In U.S. Pat. No. 5,347,950, titled Animal Litter Composition and Package, invented by Loyd G. Kasbo, James D. Cotton, Michael T. Morman and Gabriel H. Adam, there is disclosed an animal litter composition and a package for the composition. The composition constitutes decorticated flax straw which as been screened to particle sizes between about 10 and 22 U.S. Screen Mesh. The litter further includes a virucidal composition and a fragrance. The virucidal composition includes from about 0.05 to about 5 percent by weight based on the dry weight of the decorticated flax straw of a preferably anionic surfactant, and at least about 2 percent, based on the dry weight of the decorticated flax straw of at least one acid selected from a group consisting of citric, malic, and mixtures of the acids. The animal litter package constitutes a bag formed from a web of film, nonwoven/film laminates, film/paper laminate or wax/paper laminate in which the animal litter is contained prior to use. The bag can then be opened to serve as a litter box liner. Once the litter has been used, the edges of the bag can be regathered to form a bag for disposal of the litter.

The patented invention differs from the present invention because the patented invention is a compound comprising ground and uncompacted agricultural by product which can be decorticated flax straw, fax shive and a virucidal composition.

In U.S. Pat. No. 4,809,912, titled Membrane-gel Diffusion Device, invented by Thomas F. Santini, a method for the fabrication of a continuous action reservoir type air freshening device is described. The device is characterized by the use of an evaporation rate controlling porous membrane which is in intimate contact and completely covers the exposed surface of an erodible gel-type of solid perfume composition. The fragrance gel is enclosed in a container, one end of which is open and over which is affixed the porous membrane. One side of this membrane is exposed to the atmosphere; the other side intimately contacts the solid reservoir consisting of the fragrance gel. Transmission of the volatile fragrance and carrier agents to the surrounding environment through the porous membrane matrix occurs as a function of an evaporative process. The membrane permits only a limited penetration, if any by the gel solution, i.e. in the liquid state, but is sufficiently permeable to the gel solution to establish physical attachment between the solidified gel and the membrane.

The patented invention differs from the present invention because the patented invention is a reservoir treating device comprising a container with a vapor impermeable wall and opening with an evaporation rate controlling membrane extending across the opening. An erodible aqueous gel containing a volatile active ingredient cast onto the rate controlling membrane. The membrane controls the rate of release. The present invention is a chemical compound comprising a solid which contains an active ingredient within a matrix. The active ingredient migrates from the reservoir of the solid to the surface of the matrix where it absorbs and masks odors. The composition of the solid and the matrix is shown above. The rate of release is controlled by the addition of a control substance consisting of; hydrogenated castor wax, carnauba wax, montan wax, and magnesium. The present invention functions as an air freshener.

In U.S. Pat. No. 4,748,860, titled Apparatus for Determination of Insect Repellency and Attractancy, invented by Jerry F. Butler and Ira Katz, described is the use of 1-nonen-3-ol as a repellent for house flies (Musca domestica). Also described are candle compositions which may be opaque or transparent or pastel shaded which are adapted to incorporate 1-nonen-3-ol which are both perfumes and insect repellents without flashing during burning. Such compositions comprising as the basic components a mixture of (a) a hydrocarbon wax or (b) a thermoplastic polyamide resin formed from linoleic acid polymerized with a polyamide compound taken together with an alkanol amide or alkanol amine and a stearic acid compound or © a straight chain aliphatic amide in combination with light mineral oil and alcohol; compositions (a), (b) or (c), supra, taken further together with 1-nonen-3-ol taken alone or together with a perfume composition substantially inactive from an insect repellant standpoint. Also described is apparatus also referred to herein as an "olfactometer" used for measuring the repellency of said 1-nonen-3-ol. Also described herein is a process for the determination of the repellency of said 1-nonen-3-ol using said "olfactometer".

The patented invention differs from the present invention because the patented invention is a test device for determining the effectiveness of insect repellants and attractancies. It is not an air freshener substance.

In U.S. Pat. No. 4,725,282, titled Oxidative Hair Dyeing Composition Based upon a Carrier of Low Viscosity, invented by Dietrich Hock, Eugen Konrad, Gilbert Pasquier and Herbert Mager, the oxidative dyeing of human hair upon the basis of a carrier and a dye mixture dissolved therein, whereby the carrier is made from (1) 16 to 30% by weight of a mixture of (a) 0.2–5.0% by weight of at least one physiologically harmless water soluble inorganic salt, (b) 1.4–5.0% by weight sodium lauryl alcohol diglycol ether sulfate, © 0.5–6.0% by weight coconut oil acid diethanol amide, (d) 4.0–10.0% by weight of a mixture consisting of 60 to 80 parts by weight cetyl stearyl alcohol 10 to 30 parts by weight glycerin-mono-di-stearate and 0 to 20 parts by weight wool wax alcohol as well as (e) 0.1–2.0% by weight quaternized homopolymerisate of dimethyl amino ethyl methacrylate, (2) 56 to 83% by weight of water, (3) 0.1 to 5.0% by weight ammonia, (4) 0 to 5% by weight aliphatic alcohol, (5) 0 to 1% by weight perfume oil and (6) 0 to 0.5% by weight of a complex former for heavy metals. The oxidative hair dyeing composition has a relatively low viscosity, is quickly miscible with the hydrogen peroxide solution and can be easily distributed in the hair. It acts untangling and smoothing on the hair and can be easily and completely rinsed out of the hair after use. The composition does not show any thickening, even after a long time storage and it has the same end viscosity independent from the type and the amount of the dye or electrolyte addition.

The patented invention differs from the present invention because the patented invention is a composition for oxidative dying of human hair having a viscosity of 400–4000 mPa.s upon the basis of a carrier and a dye mixture dissolved therein. The present invention is an air freshener which absorbs odors.

In U.S. Pat. No. 4,696,676, titled Use of 1-nonen-3-ol for Repelling Insects, invented by Richard A. Wilson, Jerry F. Butler, Donald Withycombe, Braja D. Mookheijee, Ira Katz, and Kenneth R. Schrankel, described is the use of 1-nonen-3-ol as a repellent for house flies (Musca domestica). Also described are candle compositions which may be opaque or transparent or pastel shaded which are adapted to incorporate 1-nonen-3-ol which are both perfumes and insect repellents without flashing during burning. Such compositions comprising as the basic components a mixture of (a) a hydrocarbon wax or (b) a thermoplastic polyamide resin formed from linoleic acid polymerized with a polyamide compound taken together with an alkanol amide or alkanol amine and a stearic acid compound or © a straight chain aliphatic amide in combination with light mineral oil and alcohol; compositions (a), (b) or (c), supra, taken further together with 1-nonen-3-ol taken alone or together with a perfume composition substantially inactive from an insect repellent standpoint.

The patented invention differs from the present invention because the patented invention is a candle comprising a molded hydrocarbon wax composition having a protruding wick. The molded carbon wax consists of crystalline paraffin wax and an insect repellant perfume. The patented invention releases, by reaction with heat from a flame, an odor which is disliked by insects. The present invention is a chemical compound comprising a solid which contains an active ingredient with in a matrix. The active ingredient migrates from the reservoir of the solid to the surface of the matrix where it absorbs and masks odors. The rate of release is controlled by the addition of a control substance consisting of; hydrogenated castor wax, carnauba wax, montan wax, and magnesium. The present invention functions as an air freshener In U.S. Pat. No. 4,693,890, Titled Use of 1-nonen-3-ol for Repelling Insects, invented by Richard A. Wilson, Jerry F. Butler, Donald Withycombe, Braja D. Mookhedee, Ira Katz, and Kenneth R. Schrankel, described is the use of 1-nonen-3-ol as a repellent for house flies (Musca domestica). Also described are candle compositions which may be opaque or transparent or pastel shaded which are adapted to incorporate 1-nonen-3-ol which are both perfumes and insect repellents without flashing during burning. Such compositions comprising as the basic components a mixture of (a) a hydrocarbon wax or (b) a thermoplastic polyamide resin formed from linoleic acid polymerized with a polyamide compound taken together with an alkanol amide or alkanol amine and a stearic acid compound or © a straight chain aliphatic amide in combination with light mineral oil and alcohol; compositions (a), (b) or (c), supra, taken further together with 1-nonen-3-ol taken alone or together with a perfume composition substantially inactive from an insect repellent standpoint.

The patented invention differs from the present invention because the patented invention is a candle composition which may be opaque or transparent or pastel shaded adapted to incorporate 1-nonen-3-ol. Both of which are perfumes and insect repellents that do not flash during burning. The present invention is a chemical compound comprising a solid which contains an active ingredient with in a matrix. The active ingredient migrates from the reservoir of the solid to the surface of the matrix where it absorbs and masks odors. The present invention functions as an air freshener with out burning.

In U.S. Pat. No. D 247,573, titled Assembly for the Evaporation of an Active Volatile Substance, invented by Georg Schimanski, the ornamental design for a combined holder and mounting bracket for solid deodorant, perfume, insect repellant, is as shown and described.

The patented invention differs from the present invention because the patented invention is an ornamental design for a combined holder and mounting bracket for solid deodorant, perfume, insect repellant. The present invention is a chemical compound comprising a solid which contains an active ingredient with in a matrix.

In U.S. Pat. No. 4,070,451, titled Hoof Care Emulsion or Cream, invented by Howard Price, there is provided an improved hoof-treatment composition comprising basically and essentially an aqueous emulsion of a relatively material amount of each of a glycerol stearate, lanolin wax, lanolin alcohols, stearic acid, mineral oil, and paraffin, together with a relatively lesser amount of each of a polysorbate, sodium lauryl sulfate, a hydrolyzed animal protein, and imidazolinidyl urea. Glycerine, petrolatum, and beeswax, each in a relatively material amount, may also be included with advantage. Desirably, one or more of a lower alkyl p-hydroxy-benzoate, a coloring ingredient, a perfume ingredient, and vitamin E, each in a relatively lesser amount, may be present.

The patented invention differs from the present invention because the patented invention is a composition for treating keratinous tissues which comprises an aqueous emulsion. The present invention is a chemical compound comprising a solid which contains an active ingredient with in a matrix. The active ingredient migrates from the reservoir of the solid to the surface of the matrix where it absorbs and masks odors. The rate of release is controlled by the addition of a control substance consisting of; hydrogenated castor wax, carnauba wax, montan wax, and magnesium. The present invention functions as an air freshener.

Numerous innovations for air fresheners have been provided in the prior art that are adapted to be used. Even though these innovations may be suitable for the specific individual purposes to which they address, they would not be suitable for the purposes of the present invention as heretofore described.

SUMMARY OF THE INVENTION

The present invention is a solid containing a continuous release matrix. The matrix contains an active ingredient which is formulated to absorb objectional odors and mask them. The matrix continuous release mechanism is started by contact with the air. Because the material of the present invention is a solid it can be formed in various decorative shapes. The present invention is packaged in a bag filled with an inert gas which prevents the migration of the active ingredient from a reservoir to the surface.

The types of problems encountered in the prior art are the long term release of objectionable odors into the air within a confined space.

In the prior art, unsuccessful attempts to solve this problem were attempted namely: volatile liquids released into the air through evaporation from a wick and in a discharge of a atomized spray. However, the problem was solved by the present invention because the active ingredient is released through a migration in a matrix from a reservoir to the surface of a solid.

The present invention solved a long felt need for an air freshener that releases an active ingredient over a prolonged period of time.

Accordingly, it is an object of the present invention to provide a solid air freshener dispensing system.

More particularly, it is an object of the present invention to provide a fragrance which is released into the air from a surface of a solid.

In keeping with these objects, and with others which will become apparent hereinafter, one feature of the present invention resides, briefly stated, in a solid air freshener dispensing system containing Magnesium Silicate Hydrate.

In accordance with another feature of the present invention, a solid air freshener dispensing system contains a Saturated Monobase Acid.

Another feature of the present invention is that a solid air freshener dispensing system contains a Hydrogenated Castor Wax.

Yet another feature of the present invention is that a solid air freshener dispensing system contains a Carnuba Wax.

Still another feature of the present invention is that a solid air freshener dispensing system contains a Montan Wax.

Yet still another feature of the present invention is that a solid air freshener dispensing system contains a Metazene.

Still yet another feature of the present invention is that when exposed to ambient air the solid begins to release the active ingredient.

Another feature of the present invention is that the present invention is cast into various shapes.

Yet another feature of the present invention is that the migration controlling agent is a combination of Hydrogenated Castor, Carnuba Wax (24), Montan Wax, and Metazene (28).

Still another feature of the present invention is that the air freshener will release for up to eight weeks.

Yet still another feature of the present invention is that alcohol, and petroleum distillates are not present.

Still yet another feature of the present invention is that the solid is non-toxic and non-poisonous.

Another feature of the present invention is that the present invention is shipped in a container filled with a inert gas which retards the release mechanism.

The novel features which are considered characteristic for the invention are set forth in the appended claims. The invention itself, however, both as to its construction and its method of operation, together with additional objects and advantages thereof, will be best understood from the following description of the specific embodiments when read and understood in connection with the accompanying drawings.

BRIEF LIST OF REFERENCE NUMERALS UTILIZED IN THE DRAWING

10—solid air freshener dispensing system (10)
12—container (12)
14—inert gas (14)
16—fragrance (16)
8—Magnesium Silicate Hydrate (18)
20—Saturated Monobase Acid (20)
22—Hydrogenated Castor Wax (22)
24—Carnuba Wax (24)
26—Montan Wax (26)
28—Metazene (28)

BRIEF DESCRIPTION OF THE DRAWING

FIG. 2 is a list of ingredients for a solid air freshener dispensing system.

DESCRIPTION OF THE PREFERRED EMBODIMENT

Figure 1:
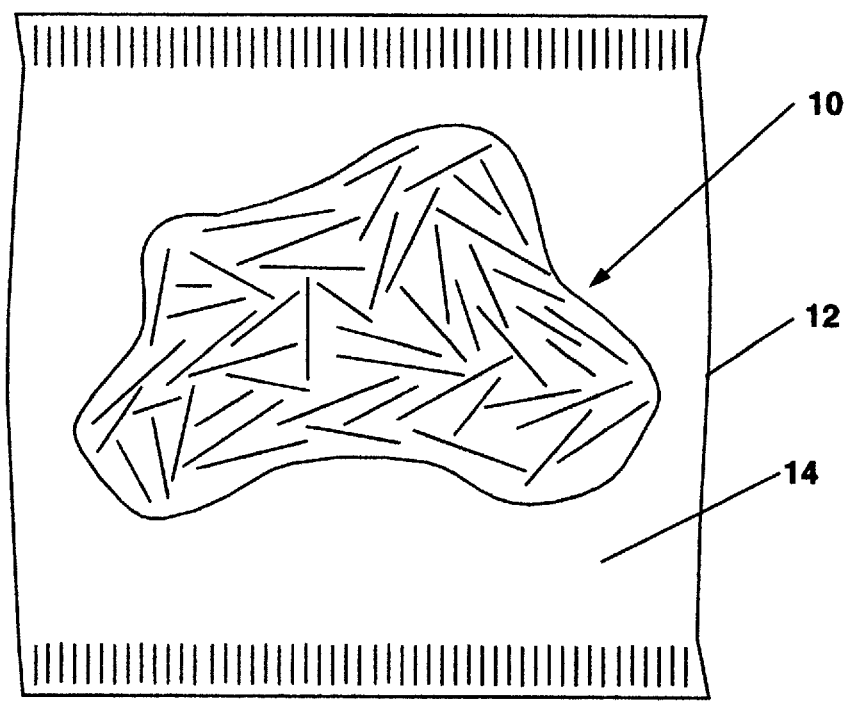
FIG. 1 is a top view of a solid air freshener dispensing system.

Firstly, referring to FIG. 1 which is a is a top view of a solid air freshener dispensing system (10) comprising a surrounding container (12). The container (12) is air proof and filled with an inert gas (14). The inert gas (14) therein functions to displace air and maintain the solid air freshener dispensing system (10) in an inactive state. The inert gas (14) is selected from a group consisting of nitrogen, helium, carbon dioxide, hydrogen, argon, nitrous oxide, and Freon.

Lastly, referring to FIG. 2 which is list of ingredients. A Magnesium Silicate Hydrate (18), Saturated Monobase Acid (20), and Metazene (28) are mixed into the wax along with a fragrance (16).

The wax proportion is preferably 31.5%. The wax proportion ranges from 20% to 40%.

The Saturated Monobase Acid (20) proportion mixed in the wax is preferably is 27.5%. The Saturated Monobase Acid (20) proportion ranges from 20% to 35%.

The Metazene (28) proportion mixed in the wax is preferably 7%. The Metazene (28) mixed in the wax ranges from 4% to 10%.

The Hydrogenated Castor Wax (22) proportion is preferably 27.5%. The Hydrogenated Castor Wax (22) proportion ranges from 20% to 40%.

The Carnuba Wax (24) proportion preferably is 3%. The Carnuba Wax (24) mixed in the wax ranges from 1% to 5%.

The Montan Wax (26) proportion preferably is 1%. The Montan Wax (26) proportion ranges from 0.1% to 2.0%.

The wax is selected from a group consisting of Hydrogenated Castor Wax (22), Carnuba Wax (24) and Montan Wax (26).

It will be understood that each of the elements described above, or two or more together, may also find a useful application in other types of constructions differing from the type described above.

While the invention has been illustrated and described as embodied in an air freshener, it is not intended to be limited to the details shown, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by letters patent is set forth in the appended claims.

1. A solid air freshener dispensing system (10) comprising:
    A) wax;
    B) Magnesium Silicate Hydrate (18) mixed into the wax; and
    C) fragrance (16) mixed into the wax.

2. The solid air freshener dispensing system (10) as described in claim 1 further comprises Saturated Monobase Acid (20) mixed in the wax.

3. The solid air freshener dispensing system (10) as described in claim 2, wherein the Saturated Monobase Acid (20) mixed in the wax is in a range from 20% to 35%.

4. The solid air freshener dispensing system (10) as described in claim 3, wherein the Saturated Monobase Acid (20) mixed in the wax is 27.5%.

5. The solid air freshener dispensing system (10) as described in claim 1 further comprises Metazene (28) mixed in the wax.

6. The solid air freshener dispensing system (10) as described in claim 5, wherein the Metazene (28) mixed in the wax is in a range from 4% to 10%.

7. The solid air freshener dispensing system (10) as described in claim 6, wherein the Metazene (28) mixed in the wax is 7%.

8. The solid air freshener dispensing system (10) as described in claim 1, wherein the wax is selected from a group consisting of Hydrogenated Castor Wax (22), Carnuba Wax (24) and Montan Wax (26).

9. The solid air freshener dispensing system (10) as described in claim 8, wherein the wax is in a range from 20% to 40%.

10. The solid air freshener dispensing system (10) as described in claim 9, wherein the is 31.5%.

11. The solid air freshener dispensing system (10) as described in claim 8, wherein the Hydrogenated Castor Wax (22) is in a range from 20% to 40%.

12. The solid air freshener dispensing system (10) as described in claim 11, wherein the wax is Hydrogenated Castor Wax (22) and is 27.5%.

13. The solid air freshener dispensing system (10) as described in claim 8, wherein the wax is Carnuba Wax (24) and is in a range from 1% to 5%.

14. The solid air freshener dispensing system (10) as described in claim 8, wherein the wax is Carnuba Wax (24) and is 3%.

15. The solid air freshener dispensing system (10) as described in claim 8, wherein the wax is Montan Wax (26) and is in a range from 0.1% to 2.0%.

16. The solid air freshener dispensing system (10) as described in claim 15, wherein the wax is Montan Wax (26) and is 1%.

17. The solid air freshener dispensing system (10) as described in claim 11 is enclosed in an air proof container (12).

18. The solid air freshener dispensing system (10) as described in claim 17, wherein the container (12) comprises an inert gas (14) therein functioning to displace air and maintain the solid air freshener dispensing system (10) in an inactive state.

19. The solid air freshener dispensing system (10) as described in claim 18, wherein the inert gas (14) is selected from a group consisting of nitrogen, helium, carbon dioxide, hydrogen, argon, nitrous oxide, and Freon.

* * * * *